United States Patent [19]

Kleiner

[11] Patent Number: 5,498,741

[45] Date of Patent: Mar. 12, 1996

[54] ALKYL ARYL ARYLPHOSPHONITES, PROCESS FOR THE PREPARATION THEREOF AND USE THEREOF

[75] Inventor: Hans-Jerg Kleiner, Kronberg/Taunus, Germany

[73] Assignee: Hoechst Aktiengesellschaft, Germany

[21] Appl. No.: 364,118

[22] Filed: Dec. 27, 1994

Related U.S. Application Data

[62] Division of Ser. No. 159,727, Dec. 1, 1993, abandoned.

[30] Foreign Application Priority Data

Dec. 3, 1992 [DE] Germany .................. 42 40 703.6

[51] Int. Cl.⁶ ......................................................... C07F 9/48
[52] U.S. Cl. ......................................................... 558/118
[58] Field of Search ............................................. 558/118

[56] References Cited

U.S. PATENT DOCUMENTS

| | | |
|---|---|---|
| 3,316,333 | 4/1967 | Hechenbleikner et al. . |
| 3,558,747 | 1/1971 | Meltsner et al. . |
| 4,385,109 | 5/1983 | Lechtken et al. . |

FOREIGN PATENT DOCUMENTS

| | | |
|---|---|---|
| 0004026 | 9/1979 | European Pat. Off. . |
| 0007508 | 2/1980 | European Pat. Off. . |
| 2944155 | 5/1980 | Germany . |
| 3139984 | 4/1983 | Germany . |
| 48-041009 | 12/1973 | Japan . |
| 56-161310 | 12/1981 | Japan . |
| 2002775 | 2/1979 | United Kingdom . |

OTHER PUBLICATIONS

Chemical Abstracts, vol. 81, No. 20, Nov. 18, 1974, Columbus Ohio, abstract No. 121856.
Chemical Abstracts, vol. 112, No. 23, Jun. 4, 1990, Columbus Ohio, abstract No. 217055.
Chemical Abstracts, vol. 97, No. 217389, JP 57105453
Chemical Abstracts, vol. 97, No. 1, Jul. 5, 1982, Columbus Ohio, abstract No. 002256.

*Primary Examiner*—Johann Richter
*Assistant Examiner*—Michael G. Ambrose
*Attorney, Agent, or Firm*—Connolly & Hutz

[57] ABSTRACT

Monoalkyl monoaryl arylphosphonites of the formula (I);

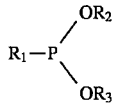

(I)

in which
$R_1$ is the radical

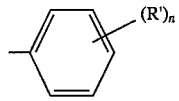

in which R' is identical or different and is $(C_1-C_6)$-alkyl, $(C_1-C_6)$-alkoxy, $(C_1-C_6)$-alkylthio, or halogen, and n is an integer from 0 to 3, or is the naphthyl radical which can bear 1 to 3 substituents R';

$R_2$ is a $(C_1-C_6)$-alkyl radical, and $R_3$ is as $R_1$, where $R_1$ and $R_2$ can be identical or different with respect to one another; is described.

4 Claims, No Drawings

ALKYL ARYL ARYLPHOSPHONITES, PROCESS FOR THE PREPARATION THEREOF AND USE THEREOF

This application is a divisional of application Ser. No. 08/159,727 filed Dec. 1, 1993 now abandoned.

Monoalkyl monophenyl alkylphosphonites are already-known. Their preparation is carried out by transesterification of dialkyl alkylphosphonites with phenol in the presence of catalytic amounts of sodium. Without use of a catalyst in this case, no transesterification occurs. The dialkyl alkylphosphonites are used in excess (2:1). Despite this, the formation of diphenyl alkylphosphonites cannot be repressed. The reaction products, as a result of a tendency to disproportionation, are difficult to purify and are apparently not storage-stable (F. W. Hoffmann et al., Am. Soc. 80,5937 [1958]).

Monoalkyl monoaryl phosphonites are therefore required which are easy to prepare, easy to purify and storage-stable. Surprisingly it has been found that monoalkyl monoaryl arylphosphonites of the formula (I) fulfill this object.

The invention therefore relates to monoalkyl monoaryl arylphosphonites of the formula (I)

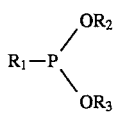  (I)

in which $R_1$ is the radical

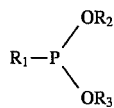

in which R' is identical or different and is $(C_1-C_6)$-alkyl, preferably $(C_1-C_4)$-alkyl, $(C_1-C_6)$-alkoxy, preferably $(C_1-C_3)$-alkoxy, $(C_1-C_6)$-alkylthio, preferably $(C_2-C_4)$-alkylthio, or halogen, preferably fluorine, chlorine or bromine and n is an integer from 0 to 3, preferably from 0 to 1, or is the naphthyl radical which can be unsubstituted or bear 1 to 3, preferably one, substituent R' (R' has the same meaning as above), $R_2$ is a $(C_1-C_6)$-alkyl radical, preferably $(C_1-C_4)$-alkyl radical, and $R_3$ is as $R_1$, where $R_2$ and $R_3$ can be identical or different with respect to one another.

Apart from the compounds (I) according to the invention used in the Examples, the following can be mentioned here by way of example:

monomethyl monophenyl phenylphosphonite,
monoethyl mono-3-methylphenyl phenylphosphonite,
mono-n-butyl mono-4-methoxyphenyl phenylphosphonite,
monoethyl mono-4-chlorophenyl phenylphosphonite,
monopropyl mono-2-tert-butylphenyl phenylphosphonite,
monoethyl monophenyl o-tolylphosphonite,
mono-n-propyl monophenyl p-tolylphosphonite,
monoethyl mono-2-methylphenyl 4-methoxyphenylphosphonite,
monoethyl monophenyl 4-methylthiophenylphosphonite,
monoethyl mono-2,4-di-tert-butylphenyl 4-methylthiophenylphosphonite,
monoethyl monophenyl 4-chlorophenylphosphonite.

The invention further relates to a process for the preparation of the compounds of the formula (I) according to the invention

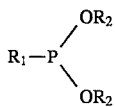  (I)

which comprises transesterifying dialkyl arylphosphonites of the formula (II)

$$R_1-P\begin{matrix}OR_2\\OR_2\end{matrix}$$  (II)

in which the radicals $R_1$ and $R_2$ have the above meaning, where the radicals $R_2$ within this meaning can be identical or different, with a phenol of the formula (III)

$$HOR_3$$  (III), in which $R_3$ has the above meaning, with elimination of the alcohols of the formula (IV)

$$HOR_2$$  (IV)

in the absence of catalysts.

It can be considered surprising that the use of catalysts is not required according to the invention. Furthermore, it is surprising that the reactions proceed virtually without formation of diaryl arylphosphonites and the compounds according to the invention are easy to purify by distillation and are storage-stable.

The dialkyl arylphosphonites of the formula (II) can easily be synthesized by simple methods (Houben-Weyl, Methoden der organischen Chemie [Methods of Organic Chemistry], Volume XII/1, page 324, 1963).

The reaction of the dialkyl arylphosphonites with the phenols of the formula (III) is preferably carried out in a molar ratio of 1:1. However, excesses both of the one and of the other component are possible; for example, the dialkyl phosphonites can be used in a molar ratio of 2:1, but also of 1:2.

In the reaction, the alcohols of the formula (IV) distill off, if required under reduced pressure, for example at 20 to 700 mbar, preferably 100 to 500 mbar. The reaction is preferably carried out in this case so that the vacuum is enhanced in the course of the reaction. The reaction is carried out at reaction temperatures from generally about 70° to 250° C., preferably about 100° to 200° C. It can be expedient in this case to increase the reaction temperature in the course of the reaction. The transesterification proceeds only slowly to completion of the reaction. It can be advantageous here to terminate the reaction after about 60 to 80% conversion and then to work up by distillation. The unreacted starting materials are recovered first in the distillation. They are then available for a fresh reaction.

The compounds (I) according to the invention are generally recovered by distillation and purified. They are storage-stable and are used as starting materials for example for the preparation of photoinitiators, fire retardants or metal extraction media.

The invention further relates to aryl aroylarylphosphinates of the formula (V)

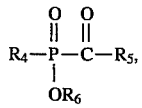  (V)

in which $R_4$ has the same meaning as $R_1$, where R' herein is preferably $(C_1-C_4)$-alkyl or $(C_1-C_3)$-alkoxy, $R_5$ is the phenyl radical unsubstituted or substituted by 1 to 3, preferably by 2 to 3, ($C_1$–$C_3$)-alkyl or ($C_1$–$C_3$)-alkoxy radicals, and $R_6$ is identical to $R_4$, where $R_4$ and $R_6$ can be identical or different with respect to one another.

Apart from the compounds (V) according to the invention mentioned in the Examples, the following can be mentioned here by way of example as further representatives:
phenyl phenyl-2-methylbenzoylphosphinate,
phenyl phenyl-2,6-dimethylbenzoylphosphinate,
2-tert-butylphenyl phenyl-2,6-dimethoxybenzoylphosphinate,
2-tert-butylphenyl phenyl-2,6-dimethylbenzoylphosphinate,
2,4-di-tert-butylphenyl phenyl-2,6-dimethylbenzoylphosphinate,
4-methylphenyl 4-methoxyphenyl-2,6-dimethylbenzoylphosphinate,
phenyl 4-methoxyphenyl-2,4,6-trimethylbenzoylphosphinate,
4-methoxyphenyl 4-methoxyphenyl-2,4,6-trimethylbenzoylphosphinate,
phenyl 4-methylphenyl-2,4,6-trimethylbenzoylphosphinate,
2-methylphenyl 4-methylphenyl-2,4,6-trimethylbenzoylphosphinate,
4-methoxyphenyl 4-methylphenyl-2,6-dimethoxybenzoylphosphinate.

The preparation of these compounds (V) succeeds for example by reaction of acid halides of the formula (VI)

(VI)

in which $R_5$ has the meaning given above and X=Br, Cl, preferably Cl, with the compounds according to the invention of the formula I with elimination of alkyl halides of the formula $R_2X$ (VII).

This reaction can be carried out without solvent or in a solvent. If solvents are used in the process according to the invention, these are aprotic and/or inert under the reaction conditions and preferably have a nonpolar character. Examples of such solvents are: N-methylpyrrolidone; dimethylformamide; ethers such as diethyl ether, tetrahydrofuran, dioxane, ethylene glycol mono- or diethers, propylene glycol mono- or diethers, butylene glycol mono- or diethers of monoalcohols having an unbranched or branched alkyl radical of 1 to 6 carbon atoms; ketones such as for example acetone, methyl ethyl ketone, methyl isopropyl ketone, methyl isobutyl ketone, cyclohexanone and similar compounds; esters such as ethyl acetate, butyl acetate, ethyl glycol acetate, methoxypropyl acetates halogenated hydrocarbons. These are preferably in this case (cyclo)aliphatic and/or aromatic hydrocarbons, such as petroleum ether, hexane, heptane, cyclohexane, toluene, the various xylenes and aromatic solvents in the boiling range from approximately 150° to 180° C. (higher boiling mineral oil fractions, such as ® Solvesso). The solvents in this case can be used individually or in a mixture.

The temperatures for carrying out the above reaction are generally between about 70° and 180° C., preferably between about 100° and 150° C. The starting materials, that is the acid halides and alkyl aryl arylphosphonites, are usually used in a molar ratio of 1:1 to 3:1, preferably in a molar ratio of 2:1. In this case, for example, the acid halides are introduced and the alkyl aryl arylphosphonires are metered in. Moreover, the addition of tertiary amines such as for example trimethylamine, triethylamine, N,N-dimethylaniline or N,N-diethylaniline in catalytic amounts is advantageous, as described for example in DE-A 31 39 984.

After elimination of the alkyl halides has been completed, if required the excess amounts of the acid halides are distilled off. The compounds of the formula (V) according to the invention remain. For purification, they are preferably distilled in vacuo. One of the advantages of these products is that they are frequently oily and non-crystalline. Such products can be handled in a particularly simple manner and can be incorporated well into paint systems. However, the crystalline products also show good solubility in paint systems. A further advantage can be seen in the fact that the cured paint systems only show a slight tendency to yellowing.

The aryl aroylarylphosphinates (V) can be used for example as photoinitiators in photopolymerizable compositions, in particular coatings, paints and printing inks.

EXAMPLE 1

Preparation of monoethyl monophenyl phenylphosphonite at atmospheric pressure 81 g (0.409 mol) of diethyl phenylphosphonite and 38.5 g (0.409 mol) of phenol were mixed and heated with stirring. At 145° C., ethanol distilled off via a small column. The temperature was gradually increased to 195° C. In total, 11 g (0.239 mol) of ethanol distilled off. The reaction mixture was then distilled. After initial runnings of 50 g, which were composed of the unreacted starting components, 54 g were obtained having a boiling point of 105° to 120° C. at 0.1 mbar. At a conversion rate of approximately 60%, the yield was 92% of theory.

$C_{14}H_{15}O_2P$ (246) Calculated: 68.29% C 6.10% H 12.60% P; Found: 68.3% C 6.05% H 12.4% P.

EXAMPLE 2

Preparation of monoethyl monophenyl phenylphosphonite under reduced pressure 118.8 g (0.6 mol) of diethyl phenylphosphonite and 56.4 g (0.6 mol) of phenol were mixed and heated with stirring at 300 to 500 mbar. At 148° C., ethanol distilled off via a small column. The internal temperature was then increased stepwise to 180° C. In total, 20 g (0.436 mol) of ethanol distilled off. The reaction mixture was then distilled. After a first fraction of 53 g, which essentially contained the unreacted starting materials, 90 g were obtained having a boiling point of 104° to 113° C. at 0.1 mbar. At a conversion rate of 73%, the yield was 84% of theory.

After a storage time of 10 months, distillation was carried out again. An unchanged product was obtained in a 95% yield.

EXAMPLE 3

Preparation of monoethyl mono-4-methylphenyl phenylphosphonite 18.8 g (0.6 mol) of diethyl phenylphosphonite and 64.9 g (0.6 mol) of p-cresol were mixed and heated at 300 to 500 mbar to 130° C. Ethanol distilled off via a small column. The temperature was increased to 165° C. stepwise, and the vacuum was simultaneously increased to 100 mbar. In total, 21 g (0.458 mol) of ethanol distilled off. The reaction mixture was then distilled. After a first fraction which contained the unreacted starting materials, 107 g were obtained having a boiling point of 118° to 120° C. at 0.1 mbar. At a 76% conversion rate, the yield was approximately 90% of theory.

$C_{15}H_{17}O_2P$ (260) Calculated: 69.23% C 6.54% H 11.92% P; Found: 69.1% C 6.50% H 11.5% P.

EXAMPLE 4

Preparation of monoethyl mono-2,4-dimethylphenyl phenylphosphonite 81 g (0.409 mol) of diethyl phenylphosphonite and 50 g (0.409 mol) of 2,4-dimethylphenol were mixed and heated at approximately 400 mbar to 135° C. Ethanol distilled off via a small column. The temperature was increased step-wise to 180° C., then the vacuum was increased to 100 mbar. In total, 16 g (0.349 mol) of ethanol distilled off. A main fraction of 79 g having a boiling point from 108° to 116° C. at 0.1 mbar was then obtained in a distillation. At an 85% conversion rate, the yield was approximately 83% of theory.

$C_{16}H_{19}O_2P$ (274) Calculated: 70.07% C 6.93% H 11.31% P; Found: 69.7% C 6.99% H 11.3% P.

EXAMPLE 5

Preparation of monoethyl mono-2,6-dimethylphenyl phenylphosphonite 64.8 g (0.327 mol) of diethyl phenylphosphonite and 40 g (0.327 mol) of 2,6-dimethylphenol were heated in vacuo at approximately 350 mbar to 165° C. At this temperature, ethanol distilled off slowly. In the course of 8 hours, the temperature was slowly increased to 185° C., and the vacuum was increased to 100 mbar. In total, 12 g (0.26 mol) of ethanol were eliminated. The reaction mixture was then distilled. After a first fraction, which contained the starting components, 63 g were obtained having a boiling point of 116° C. at 0.2 mbar. At a conversion rate of 80%, the yield was 88% of theory.

$C_{16}H_{19}O_2P$ ( 274 ) Calculated: 70.07% C 6.93% H 11.31% P; Found: 69.5% C 6.88% H 11.1% P.

EXAMPLE 6

Preparation of monoethyl mono-2,5-dimethylphenyl phenylphosphonite 81 g (0.409 mol) of diethyl phenylphosphonite and 50 g (0.409 mol) of 2,5-dimethylphenol were heated with stirring in vacuo at 400 mbar to 145° C. Ethanol distilled off via a small column during this. The temperature was then increased stepwise to 180° C., and the vacuum was increased to 100 mbar. In total, 15.4 g (0.355 mol) of ethanol distilled off. The reaction mixture was then distilled. After initial runnings which contained the starting materials, 76 g were obtained having a boiling point of 114° C. at 0.1 mbar. At an 82% conversion rate, the yield was 83% of theory.

$C_{16}H_{19}O_2P$ (274) Calculated: 70.07% C 6.93% H 11.31% P; Found: 70.1% C 6.85% H 11.4% P.

EXAMPLE 7

Preparation of monoethyl mono-2,4,6-trimethylphenyl phenylphosphonite 61.3 g (0.31 mol) of diethyl phenylphosphonite and 50.0 g (0.367 mol) of 2,4,6-trimethylphenol were heated with stirring at 200 mbar to 180° to 200° C.; 10.5 g (0.228 mol) of ethanol distilled off via a Vigreux column. After the reaction was completed, the reaction mixture was distilled. 55 g were obtained having a boiling point of 135° C. at 0.2 mbar. This corresponds to a yield of 85% of theory, based on the amount of ethanol eliminated.

$C_{17}H_{21}O_2P$ (288) Calculated: 70.83% C 7.29% H 10.76% P; Found: 70.5% C 7.3% H 10.8% P.

EXAMPLE 8

Preparation of phenyl phenyl-2,4,6-trimethylbenzoylphosphinate 96.4 g (0.528 mol) of 2,4,6-trimethylbenzoyl chloride and 1.2 g of triethylamine were heated to 115° C. and 65 g (0.264 mol) of monoethyl monophenyl phenylphosphonite were added dropwise in 75 minutes under a nitrogen atmosphere and with vigorous stirring. Ethyl chloride was given off as gas and was condensed in a downstream cold trap. The mixture was then further stirred for 2 hours at 115° C. and simultaneously a relatively strong nitrogen stream was passed through the apparatus. In total, at the end of the reaction 16 g (94% of theory) of ethyl chloride were situated in the cold trap. The excess 2,4,6-trimethylbenzoylchloride was then distilled off at 1 mbar and the residue was distilled with the aid of a thin-film evaporator (bath temperature: 230° C.; 0.3 mbar). 78 g were obtained. The yield was 81% of theory.

$C_{22}H21O_3P$ (364) Calculated: 72.53% C 5.77% H 8.52% P; Found: 72.3% C 5.81% H 8.5% P.

EXAMPLE 9

Preparation of 4-methylphenol phenyl-2,4,6-trimethylbenzoylphosphinate 65.3 g (0.358 mol) of 2,4,6-trimethylbenzoyl chloride and 0.6 g of triethylamine were heated to 115° C. and 46.5 g (0.179 mol) of monoethyl mono-4-methylphenyl phenylphosphonite were added dropwise in one hour under a nitrogen atmosphere and with vigorous stirring. Ethyl chloride was given off as a gas and was condensed in a downstream cold trap. The mixture was then further stirred at 115° C. for 2 hours under an intensified nitrogen stream. In total, 10.5 g of ethyl chloride (91% of theory) were obtained. The excess 2,4,6-trimethylbenzoyl chloride was then distilled off, and the residue was distilled with the aid of a thin-film evaporator (bath temperature: 230° C.; 0.2 mbar). 57 g were obtained. The residue was 84% of theory. The product thus obtained could then be distilled in a standard distillation apparatus at 0.3 mbar (217° to 219° C.), the product crystallizing in the receiver. Recrystallization from cyclohexane: melting point: 114° to 116° C.

$C_{23}H_{23}O_3P$ (378) Calculated: 73.02% C 6.09% H 8.20% P; Found: 72.9% C 6.00% H 8.1% P.

EXAMPLE 10

Preparation of 2,4-dimethylphenyl phenyl-2,4,6-trimethylbenzoylphosphinate 79.9 g (0.438 mol) of 2,4,6-trimethylbenzoyl chloride and 1 g of triethylamine were heated under a nitrogen atmosphere to 115° C. and 60 g (0.219 mol) of monoethyl mono-2,4-dimethylphenyl phenylphosphonite were added dropwise in one hour with vigorous stirring. Ethyl chloride was given off as a gas and condensed in a downstream cold trap. The mixture was then further stirred for 2 hours at 115° C. under an intensified nitrogen stream. In total, 14 g of ethyl chloride (99% of theory) were obtained. The excess acid chloride was then distilled off, and the remaining residue was distilled with the aid of a thin-film evaporator (bath temperature: 240° C.; 0.2 mbar). 63 g were obtained. The yield was 74% of theory. The product crystallized and was recrystallized from isopropanol. Melting point: 78° to 80° C.

$C_{24}H_{25}O_3P$ (392) Calculated: 73.47% C 6.38% H 7.91% P; Found: 73.2% C 6.28% H 7.5% P.

EXAMPLE 11

Preparation of 2,6-dimethylphenyl phenyl-2,4,6-trimethylbenzoylphosphinate

The product was prepared analogously to Example 10. Distillation with the aid of a thin-film evaporator (bath temperature: 235° C.; 0.3 mbar). The yield was 61% of theory.

$C_{24}H_{25}O_3P$ (392) Calculated: 73.47% C 6.38% H 7.91% P; Found: 73.4% C 6.21% H 7.9% P.

EXAMPLE 12

Preparation of 2,5-dimethylphenyl phenyl-2,4,6-trimethylbenzoylphosphinate

The product was prepared analogously to Example 10. Distillation with the aid of a thin-film evaporator (bath temperature: 230° C.; 0.1 mbar). The yield was 73% of theory.

$C_{24}H_{25}O_3P$ (392) Calculated: 73.47% C 6.38% H 7.91% P; Found: 73.4% C 6.30% H 7.4% P.

EXAMPLE 13

Preparation of 2,4,6-trimethylphenyl phenyl-2,4,6-trimethylbenzoylphosphinate 44.4 g (0.243 mol) of 2,4,6-trimethylbenzoyl chloride and 0.5 g of triethylamine were heated under a nitrogen atmosphere to 115° C. and 35 g (0.1215 mol) of monoethyl mono-2,4,6-trimethylphenyl phenylphosphonite were added dropwise in one hour with vigorous stirring. Ethyl chloride was given off as a gas and condensed in a downstream cold trap. The mixture was further stirred for 2 hours at 115 to 120° C. under an intensified nitrogen stream. In total, 7.5 g of ethyl chloride (95% of theory) condensed. The excess acid chloride was then distilled off and the remaining residue was distilled with the aid of a thin-film evaporator (bath temperature: 230° C.; 0.2 mbar). 37 g were obtained. This is a yield of 75% of theory. The product crystallized. Recrystallization from isopropanol: melting point: 94° to 96° C.

$C_{25}H_{27}O_3P$ (406) Calculated: 73.89% C 6.65% H 7.64% P; Found: 73.8% C 6.55% H 7.7% P.

EXAMPLE 14

Preparation of monoethyl mono-4-methoxyphenyl phenylphosphonite 99 g (0.5 mol) of diethyl phenylphosphonite and 62 g (0.5 mol) of 4-methoxyphenol were mixed and heated with stirring at 415 mbar. Ethanol distilled off at 115° C. via a small column. The temperature was then increased stepwise to 160° C., and the vacuum was simultaneously increased to 70 mbar. In total, 21.5 g (0.467 mol) of ethanol distilled off. The batch was then cooled and distilled. After a first fraction of 29 g, which essentially contained the unreacted starting materials, 103 g were obtained having a boiling point from 135° to 138° C. at 0.1 to 0.2 mbar. The yield was thus 75% of theory.

$C_{16}H_{17}O_3P$ (276) Calculated: 65.22% C 6.16% H 11.23% P; Found: 65.1% C 6.2% H 10.9% P.

EXAMPLE 15

Preparation of 4-methoxyphenyl phenyl-2,4,6-trimethylbenzoylphosphinate 59.5 g (0.326 mol) of 2,4,6-trimethylbenzoyl chloride and 0.75 g of triethylamine were heated to 115° C. and 45 g (0.163 mol) of monoethyl mono-4-methoxyphenyl phenylphosphonite were added dropwise in one hour under a nitrogen atmosphere and with vigorous stirring. Ethyl chloride was given off as a gas and was condensed in a downstream cold trap. The mixture was then further stirred at 110° to 115° C. for 90 minutes. In total, at the end of the reaction, 9 g (88% of theory) of ethyl chloride were situated in the cold trap. The excess 2,4,6-trimethylbenzoyl chloride was then distilled off at 1 mbar and the residue was distilled with the aid of a thin-film evaporator (bath temperature: 260° C.; 0.4 mbar). 40 g were obtained. The yield was 65% of theory.

$C_{23}H_{33}O_3P$ (378) Calculated: 65.40% C 8.73% H 8.20% P; Found: 65.5% C 8.8% H 8.1% P.

EXAMPLE 16

Preparation of monoethyl mono-2-tert-butylphenyl phenylphosphonite 99 g (0.5 mol) of diethyl phenylphosphonite and 75 g (0.5 mol) of 2-tert-butylphenol were mixed and heated with stirring at 530mbar to 170° C. Ethanol distilled off during this via a small column. The temperature was then increased stepwise to 180° C., and the vacuum was simultaneously enhanced to 100mbar. After 16 hours, a total of 18 g of ethanol distilled off. The batch was then cooled and distilled. After a first fraction, which contained the unreacted starting materials, 116 g were obtained having a boiling point of 139° C. at 0.1 mbar. The yield was thus for a 78% conversion rate almost 100% of theory.

$C_{18}H_{23}O_2P$ (302) Calculated: 71.52% C 7.82% H 10.27% P; Found: 71.5% C 7.5% H 9.9% P.

EXAMPLE 17

Preparation of 2-tert-butylphenyl phenyl-2,4,6-trimethylbenzoylphosphinate 69.7 g (0.382 mol) of 2,4,6-trimethylbenzoyl chloride and 0.9 g of triethylamine were heated under a nitrogen atmosphere to 115° C. and 57.8 g (0.191 mol) of monoethyl mono-2-tert-butylphenyl phenylphosphonite were added dropwise in one hour with stirring. Ethyl chloride was given off as a gas and was condensed in a downstream cold trap. The mixture was further stirred for 2 hours. In total, 11.7 g of ethyl chloride (95% of theory) condensed. After distilling off the excess acid chloride, the residue was distilled with the aid of a thin-film evaporator (bath temperature: 270° C.; 0.4 mbar). 70 g were obtained. The product was brought to crystallization from concentrated acetone solution, melting point: 76°–79° C. The yield was 87% of theory.

$C_{26}H_{29}O_3P$ (420) Calculated: 74.29% C 6.91% H 7.38% P; Found: 74.1% C 6.9% H 7.4% P.

EXAMPLE 18

Preparation of monoethyl mono-2,4-di-tert-butylphenyl phenylphosphonite 79.2 g (0.4 mol) of diethyl phenylphosphonite and 82.5 g (0.4 mol) of 2,4-di-tert-butylphenol were heated to 160° C. at 400mbar. Ethanol began to distill off during this via a small column. The temperature was then increased stepwise to 180°–190° C. at 150–200 mbar. After 20 hours, a total of 14 g of ethanol distilled off. After cooling, the mixture was distilled. After a first fraction, which contained unreacted starting materials, 70 g were obtained having a boiling point of 149° C. at 0.1 mbar. The yield was thus at a 76% conversion rate 64% of theory.

$C_{22}H_{31}O_2P$ (358) Calculated: 73.74% C 8.66% H 8.66% P; Found: 73.5% C 8.7% H 8.5% P.

EXAMPLE 19

Preparation of 2,4-di-tert-butylphenyl phenyl-2,4,6-trimethylbenzoylphosphinate 50.4 g (0.276 mol) of 2,4,6-trimethylbenzoyl chloride and 0.6 g of triethylamine were heated under a nitrogen atmosphere to 115° C. and 49.4 g (0.138 mol) of monoethyl mono-2,4-di-tert-butylphenyl phenylphosphonite were added dropwise in one hour with stirring. Ethyl chloride was given off as a gas and was condensed in a downstream cold trap. The mixture was then further stirred for 2 hours. In total, 8.5 g of ethyl chloride (96% of theory) condensed. After distilling off excess acid chloride, little acetone was added to the residue after cooling. After crystallization, 42 g were obtained having a melting point of 107°14 110° C. The yield was thus 64% of theory.

$C_{30}H_{37}O_3P$ (476) Calculated: 75.63% C 7.77% H 6.51% P; Found: 75.6% C 7.5% H 6.3% P.

EXAMPLE 20

Preparation of monoethyl monophenyl 4-methoxyphenylphosphonite 113 g (0.496 mol) of diethyl 4-methoxyphenylphosphonite and 46.6 g (0.496 mol) of phenol were mixed and heated with stirring to 110° C. at 350–400 mbar. Ethanol distilled off during this via a small column. The temperature was then increased stepwise to 150° C., and the vacuum was simultaneously increased to 100 mbar. After completion of the reaction, the batch was cooled and distilled. 105 g were obtained having a boiling point of 159° C. at 0.4 mbar. The yield was thus 77% of theory.

$C_{15}H_{17}O_3P$ (278) Calculated: 65.22% C 6.16% H 11.23% P; Found: 65.2% C 6.1% H 11.0% P.

EXAMPLE 21

Preparation of phenyl 4-methoxyphenyl-2,4,6-trimethylbenzoylphosphinate 46.3 g (0.2538 mol) of 2,4,6-trimethylbenzoyl chloride and 0.6 g of triethylamine were heated under a nitrogen atmosphere to 115° C. and 35 g (0.127 mol) of monoethyl monophenyl 4-methoxyphenylphosphonite were added dropwise in 40 minutes with stirring. Ethyl chloride was given off as a gas. After further stirring for 2 hours, after distilling off the excess acid chloride, the residue was distilled with the aid of a thin-film evaporator (bath temperature: 255° C.; 0.2 mbar). 42 g of a yellowish oil were obtained. The yield was 84% of theory.

$C_{23}H_{23}O_4P$ (394) Calculated: 70.05% C 5.84% H 7.87% P; Found: 70.1% C 5.75% H 7.8% P.

I claim:

1. A process for the preparation of the monoalkyl monoaryl arylphosphonite of the formula (I)

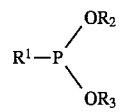 (I)

in which $R_1$ is the radical

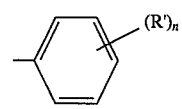

in which R' is identical or different and is $(C_1–C_6)$-alkyl, $(C_1–C_6)$-alkoxy, $(C_1–C_6)$-alkylthio, or halogen, and n is an integer from 0 to 3, or is the naphthyl radical which can be unsubstituted or bear 1 to 3 substituents R', $R_2$ is a $(C_1–C_6)$-alkyl radical, and $R_3$ is as $R_1$, where $R_1$ and $R_3$ can be identical or different with respect to one another, which comprises transesterifying dialkyl arylphosphonies of the formula (II)

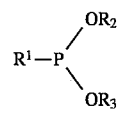 (I)

in which the radicals $R_1$ and $R_2$ have the above meaning, where the radicals $R_2$ within this meaning can be identical or different, with a phenol of the formula (III)

 (III)

in which $R_3$ has the above meaning, with elimination of the alcohols of the formula (IV)

 (IV)

in the absence of catalysts.

2. The process as claimed in claim 1, wherein the transesterification takes place at a molar ratio of the compounds (II) and (III) of 2:1 to 1:2.

3. The process as claimed in claim 2, wherein the molar ratio of (II) to (III) is 1:1.

4. The process as claimed in claim 1, wherein the transesterification is carried out at temperatures of 70° to 250° C.

* * * * *